United States Patent
Shinkawa et al.

(10) Patent No.: US 9,688,974 B2
(45) Date of Patent: *Jun. 27, 2017

(54) ASPERGILLUS MUTANT STRAIN

(71) Applicant: HONDA MOTOR CO., LTD., Tokyo (JP)

(72) Inventors: Satoru Shinkawa, Wako (JP); Shigenobu Mitsuzawa, Wako (JP); Maiko Tanaka, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/600,098

(22) Filed: Jan. 20, 2015

(65) Prior Publication Data
US 2015/0203832 A1 Jul. 23, 2015

(30) Foreign Application Priority Data

Jan. 22, 2014 (JP) ................. 2014-009747

(51) Int. Cl.
*C12N 9/24* (2006.01)
*C12N 1/15* (2006.01)
*C12N 15/80* (2006.01)
*C12P 21/02* (2006.01)
*C12N 9/42* (2006.01)
*C12R 1/69* (2006.01)

(52) U.S. Cl.
CPC ......... *C12N 9/2437* (2013.01); *C12N 9/2402* (2013.01); *C12N 9/2405* (2013.01); *C12N 9/248* (2013.01); *C12N 9/2434* (2013.01); *C12N 9/2445* (2013.01); *C12N 9/2482* (2013.01); *C12N 15/80* (2013.01); *C12P 21/02* (2013.01); *C12R 1/69* (2013.01)

(58) Field of Classification Search
None
See application file for complete search history.

(56) References Cited

U.S. PATENT DOCUMENTS

2004/0253702 A1* 12/2004 Fidantsef ............ A61K 36/062 435/209
2013/0059353 A1* 3/2013 McFarland ........ C12N 15/8243 435/145

OTHER PUBLICATIONS

Jin et al., Adenine auxotrophic mutants of Aspergilus oryzae: development of a novel transformation system with triple auxotrophic hosts, Biosci. Biotechnol. Biochem., 2004, 68, 656-662.*
Maruyama et al., Chapter 27: Targeted gene disruption in koji mold Aspergillus oryzae, Methods in Molecular Biology, 2011, 765, 447-56.*
Toda et al., Deletion analysis of the enolase (enoA) promoter from the filamentous fungus Aspergillus oryzae, Curr. Genet., 2001, 40, 260-67.*
Chang et al., Effect of steam explosion and microbial fermentation on cellulose and lignin degradation of corn stover, Bioresource Tech., 2012, 104, 587-92.*
Ruiz-Diez, Strategies for transformation of filamentous fungi, J. Appl. Microbiol., 2002, 92, 189-195.*
Contribution Ratios of amyA, amyB, amyC Genes to High-Level a-Amylase Expression in Aspergillus oryzae, Takashi Nemoto et al., Bioscience, Biotechnology, and Biochemistry, 2012, vol. 76(8), pp. 1477-1483, Discussed in specification, English text.
Transformation System for Aspergillus oryzae with Double Auxotrophic Mutations, niaD and sC, Osamu Yamada et al., Bioscience, Biotechnology, and Biochemistry, 1997, vol. 61(8), pp. 1367-1369, Discussed in specification, English text.
The development of a homologous transformation system for Aspergillus oryzae based on the nitrate assimilation pathway: A convenient and general selection system for filamentous fungal transformation, Mol. Gen. Genet., vol. 218, pp. 99-104, (1989), Discussed in specification, English text.
U.S. Office Action dated Jun. 4, 2015, U.S. Appl. No. 14/600,103, 10 pages.
U.S. Notice of Allowance dated Oct. 21, 2015, U.S. Appl. No. 14/600,103, 7 pages.
Takahashi, et al. "Development of an efficient gene-targeting system in Aspergillus luchuensis by deletion of the non-homologous end joining system", Journal of Bioscience and Bioengineering, 2011, vol. 112(6), p. 529-534, 6 pages.
Mizutani, et al., "A defect of LigD (human Lig4 homolog) for nonhomologous end joining signifcantly improves efficiency of gene-targeting in Aspergillus oryzae", Fungal Genetics and Biology, 2008, vol. 45, p. 878-889, 12 pages.
Murayama, et al., "Multiple gene disruptions by marker recycling with highly efficient gene-targeting background (Δlig D) in Aspergillus oryzae", Biotechnol Lett, 2008, 30, 1811-1817, 7 pages.

* cited by examiner

*Primary Examiner* — Robert Mondesi
*Assistant Examiner* — Todd M Epstein
(74) *Attorney, Agent, or Firm* — Rankin, Hill & Clark LLP

(57) ABSTRACT

An *Aspergillus* mutant strain characterized in that it is an auxotrophic mutant strain of *Aspergillus oryzae* strain AOK27L.

4 Claims, 3 Drawing Sheets

ASPERGILLUS MUTANT STRAIN

TECHNICAL FIELD

The present invention relates to an *Aspergillus* mutant strain which is suitable for solid culture and is also suitable as a host for genetic recombination, a transformant obtained from the *Aspergillus* mutant strain, and a method of producing a saccharifying enzyme using the transformant.

Priority is claimed on Japanese Patent Application No. 2014-009747, filed Jan. 22, 2014, the content of which is incorporated herein by reference.

BACKGROUND ART

In addition to environmental problems such as global warming and air pollution, from concerns related to the energy supply for transport such as the significant increase in crude oil prices and crude oil depletion expected in the near future (peak oil), in recent years, development of alternative energy to petroleum is a very important issue. Cellulose-based biomass, such as plant biomass and lignocellulose, which is the most abundant renewable energy source on the earth, is expected as an alternative resource to petroleum.

By culturing an *Aspergillus* fungus (koji mold) producing a saccharifying enzyme on the surface of the solid biomass such as rice straw and corn stover, it is possible to subject the biomass to a saccharification treatment. By using a transformant obtained by introducing a gene for a saccharifying enzyme with higher saccharification capability into an *Aspergillus* strain, it is possible to improve the efficiency of the saccharification treatment.

On the other hand, when introducing a foreign gene into a microorganism such as an *Aspergillus* strain for transformation, in order to selectively pick only microorganisms into which the foreign gene of interest has been introduced, a method of using an auxotrophic strain as a host which is deleted for pyrG gene (orotidine-5'-phosphate decarboxylase), sC gene, niaD gene and the like has been generally used (see, for example, Non-Patent Document 1 or 2). For example, when using a strain that became auxotrophic for uridine due to deletion of the pyrG gene as a host strain and culturing in a uridine-free medium after introducing thereinto a combination of the gene of interest and the pyrG gene, since only transformants are able to grow, it is possible to efficiently select genetically modified fungi.

PRIOR ART DOCUMENTS

Non-Patent Documents

[Non-Patent Document 1] Nemoto, et. al., Bioscience, Biotechnology, and Biochemistry, 2012, vol. 76 (8), p. 1477-1483.
[Non-Patent Document 2] Yamada, et. al., Bioscience, Biotechnology, and Biochemistry, 1997, vol. 61 (8), p. 1367-1369.

SUMMARY OF THE INVENTION

Problems to be Solved by the Invention

The present invention has an object of providing an *Aspergillus* mutant strain which is suitable for solid culture using herbaceous biomass, and is also suitable as a host for genetic recombination; a transformant obtained by introducing a saccharifying enzyme gene into the *Aspergillus* mutant strain; and a method of producing a saccharifying enzyme using the transformant.

Means for Solving the Problems

An *Aspergillus* mutant strain, a transformant and a method of producing a saccharifying enzyme according to the present invention include the following aspects [1] to [9].

[1] An *Aspergillus* mutant strain which is an auxotrophic mutant strain of *Aspergillus oryzae* strain AOK27L.

[2] The *Aspergillus* mutant strain according to the aforementioned aspect [1] which has a completely or partially deleted pyrG gene and is auxotrophic for uridine.

[3] The *Aspergillus* mutant strain according to the aforementioned aspect [1] which is an *Aspergillus oryzae* strain H01 (accession number: NITE BP-01749).

[4] A transformant obtained by introducing a pyrG gene and a saccharifying enzyme gene into the *Aspergillus* mutant strain described in any one of the aforementioned aspects [1] to [3].

[5] The transformant according to the aforementioned aspect [4], wherein the aforementioned saccharifying enzyme gene is at least one gene selected from the group consisting of a cellobiohydrolase gene, a β-glucosidase gene, an endoxylanase gene, an arabinofuranosidase gene, a glucuronidase gene and an endoglucanase gene.

[6] The transformant according to the aforementioned aspect [4], wherein the aforementioned saccharifying enzyme gene is at least one gene selected from the group consisting of a cellobiohydrolase gene derived from *Acremonium cellulolyticus*, a β-glucosidase gene derived from *Acremonium cellulolyticus*, an endoxylanase gene derived from a fungus belonging to the genus *Thermoascus*, an arabinofuranosidase gene derived from *Acremonium cellulolyticus* and a glucuronidase gene derived from *Acremonium cellulolyticus*.

[7] The transformant according to any one of the aforementioned aspects [4] to [6], wherein the pyrG gene and the aforementioned saccharifying enzyme gene are incorporated into a chromosome.

[8] A method of producing a saccharifying enzyme, the method including culturing the transformant described in any one of the aforementioned aspects [4] to [7] by solid culturing.

[9] The method of producing a saccharifying enzyme according to the aforementioned aspect [8], wherein the solid culturing is carried out using rice straw or corn stover.

Effects of the Invention

Since the *Aspergillus* mutant strain according to the present invention is suitable for solid culture and is also an auxotrophic strain, it is suitable as a host for genetic recombination for introducing a foreign gene. For this reason, a transformant obtained by introducing a saccharifying enzyme gene into the *Aspergillus* mutant strain is capable of producing a saccharifying enzyme efficiently by solid culture.

BEST MODE FOR CARRYING OUT THE INVENTION

<*Aspergillus* Mutant Strain>

Figure 1:
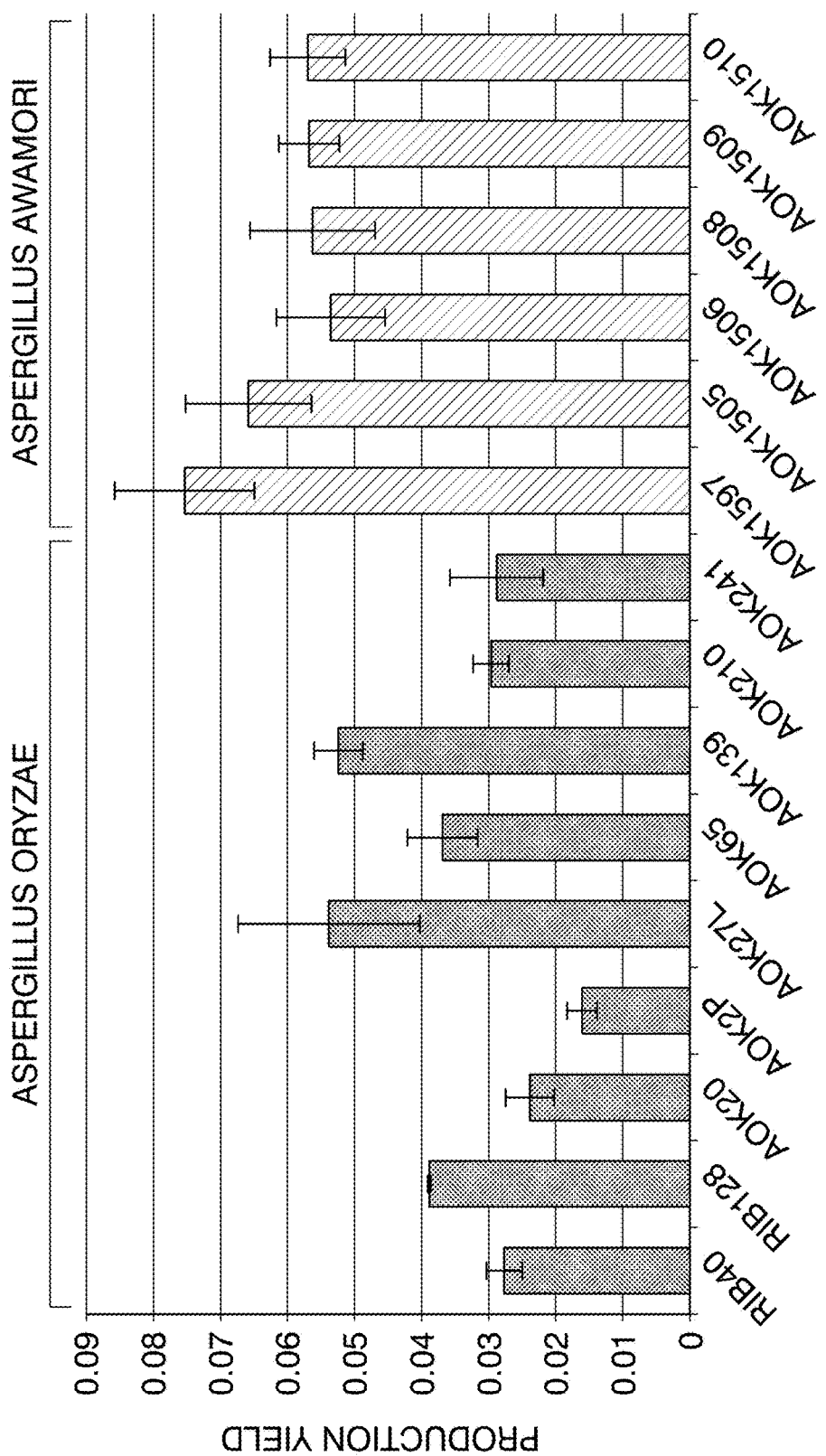
FIG. 1 is a diagram showing the measurement results of the enzyme production yield of each strain belonging to *Aspergillus oryzae* or *Aspergillus awamori* in Reference Example 1.

An *Aspergillus* mutant strain according to the present invention is characterized in that it is an auxotrophic mutant strain of the *Aspergillus oryzae* strain AOK27L (available from Akita Konno Co., Ltd.) (hereinafter, abbreviated as the "AOK27L strain" at times) which is obtained by deleting the function of a specific gene involved in the synthesis of a specific nutrient and the like. In the present invention, the term simply "auxotrophic" means the property which requires a specific nutrient.

As shown in Reference Example 1 to be described later, the AOK27L strain is superior to other strains of *Aspergillus oryzae* in terms of the enzyme production efficiency when cultured on a solid medium. In other words, the *Aspergillus* mutant strain according to the present invention is a strain obtained by conferring auxotrophy to a strain originally exhibiting high enzyme production efficiency in solid culture.

In addition, the *Aspergillus* mutant strain according to the present invention exhibits auxotrophy. For this reason, by using the *Aspergillus* mutant strain according to the present invention as a host for genetic recombination, it is possible to obtain a genetically modified strain efficiently. As the auxotrophy exhibited by the mutant strain of *Aspergillus* according to the present invention, auxotrophy for uridine is preferred.

In order to confer auxotrophy to the AOK27L strain, a gene involved in the synthesis of a nutrient or the like is completely or partially deleted. For example, in order to confer auxotrophy for uridine to the AOK27L strain, the pyrG gene is completely or partially deleted. In addition, the sC gene or niaD gene may be completely or partially deleted. The method for completely or partially deleting the pyrG gene and the like is not particularly limited, and can be suitably selected and used from amongst known techniques in the genetic recombination of microbes, such as a protoplast-PEG method and a natural mutagenesis method.

In other words, the auxotrophic mutant strain of AOK27L strain according to the present invention includes an *Aspergillus* mutant strain which is deleted completely or partially a gene involved in the synthesis of a nutrient or the like by the artificial genetic recombination.

The term "partially deleted" means that a deletion of a gene, such as an enzyme catalytic function is lost. As the deletion, for example, a deletion of an initiation codon of a gene, an introduction of a stop codon into the middle of a gene and the like can be mentioned.

The *Aspergillus* mutant according to the present invention can be cultured with the same culture medium and culture conditions as those for the AOK27L strain with the exception that the culture medium is added with a required nutrient (medium supplemented with uridine in the case of uridine auxotrophy).

<Transformant>

A transformant obtained by introducing a saccharifying enzyme gene into the *Aspergillus* mutant according to the present invention is capable of producing the saccharifying enzyme highly efficiently. By introducing a gene deleted from the AOK27L strain in order to confer auxotrophy together with the saccharifying enzyme gene at the time of producing the transformant, a strain into which the saccharifying enzyme gene has been introduced can be obtained efficiently by using the presence and absence of auxotrophy as an indicator.

When the *Aspergillus* mutant according to the present invention is auxotrophic for uridine, the transformant according to the present invention is characterized in that the pyrG gene and the saccharifying enzyme gene have been introduced. By introducing both the pyrG gene and the saccharifying enzyme gene, it becomes possible to grow the transformant even in a uridine-free medium. Therefore, by culturing the *Aspergillus* strains after gene introduction in a uridine-free medium, it is possible to select only transformants.

In the transformant according to the present invention, although the pyrG gene and the saccharifying enzyme gene may be maintained as extrachromosomal genes outside the chromosome, in terms of expression stability of the saccharifying enzyme, those that are integrated into the chromosome are more preferred.

For example, by introducing an expression vector incorporating an expression cassette for expressing the pyrG gene and an expression cassette for expressing the saccharifying enzyme gene into the aforementioned *Aspergillus* mutant strain, a transformant can be obtained. It should be noted that although both of an expression vector incorporating the expression cassette for expressing the pyrG gene and an expression vector incorporating the expression cassette for expressing the saccharifying enzyme gene may be introduced into the *Aspergillus* mutant, in terms of selection accuracy by uridine auxotrophy, it is more preferable to carry out a transformation process by placing the expression cassettes of both genes on a single expression vector.

In other words, a method of producing a transformant according to the present invention may include introducing an expression vector incorporating an expression cassette for expressing the pyrG gene and an expression cassette for expressing the saccharifying enzyme gene into the aforementioned *Aspergillus* mutant strain; or may include introducing both of an expression vector incorporating the expression cassette for expressing the pyrG gene and an expression vector incorporating the expression cassette for expressing the saccharifying enzyme gene m into the aforementioned *Aspergillus* mutant strain.

Here, the expression cassette refers to a combination of DNA required for expressing a structural gene (a gene which determines the primary structure of a protein, namely, the amino acid sequence) and contains the structural gene and a promoter and terminator that function inside the host cell. The expression cassette may further include either one or more of a 5'-untranslated region and 3'-untranslated region. In addition, the expression cassette for expressing the pyrG gene and the expression cassette for expressing the saccharifying enzyme gene may be separate expression cassettes, or both the pyrG gene and the saccharifying enzyme gene may be included within a single expression cassette as the structural genes.

Further, as an expression vector for incorporating the expression cassette, it is possible to use those that are selected appropriately from the known vectors that can be used for the transformation of *Aspergillus* strains, including *Aspergillus oryzae*, and that are modified appropriately if needed.

The transformation method that introduces the expression vector into the *Aspergillus* mutant strain according to the present invention is not particularly limited, and can be carried out by various methods used for introducing genes to the *Aspergillus* strains, including *Aspergillus oryzae*. As the transformation method, for example, a protoplast-PEG method, a PEG-calcium method (Mol. Gen. Genet., Vol. 218, p. 99-104 (1989)), an electroporation method, an *Agrobacterium* method and the like can be mentioned. By culturing on a uridine-free medium following transformation, only the transformant into which the expression cassette has been introduced is grown and selected.

As a saccharifying enzyme gene to be introduced into the *Aspergillus* mutant strain according to the present invention, a gene encoding a saccharifying enzyme used in the saccharification of cellulose-based biomass, such as plant biomass and lignocellulose is generally preferred. As the saccharifying enzyme gene, for example, an endoglucanase of glucoside hydrolase (cellulase or endo-1,4-β-D-glucanase, EC 3.2.1.4) gene, an exo-type cellobiohydrolase (1,4-β-cellobiosidase or cellobiohydrolase, EC 3.2.1.91) gene, a β-glucosidase (EC 3.2.1.21) gene, a xylanase (endo-1,4-β-xylanase, EC 3.2.1.8) gene serving as a hemicellulase, an arabinofuranosidase (EC 3.2.1.55) gene, a glucuronidase (EC 3.2.1.31) gene and the like can be mentioned. The saccharifying enzyme gene to be introduced into the *Aspergillus* mutant strain according to the present invention may be only one type, or a combination of two or more types may be introduced.

As a saccharifying enzyme gene to be introduced into the *Aspergillus* mutant strain according to the present invention, a gene encoding a saccharifying enzyme exhibiting a strong saccharification capacity is preferred. For example, it is preferable to introduce one type or a combination of two or more types of genes selected from the group consisting of a cellobiohydrolase gene derived from *Acremonium cellulolyticus*, a β-glucosidase gene derived from *Acremonium cellulolyticus*, an endoxylanase gene derived from a fungus belonging to the genus *Thermoascus*, an arabinofuranosidase gene derived from *Acremonium cellulolyticus* and a glucuronidase gene derived from *Acremonium cellulolyticus*.

As a saccharifying enzyme gene to be introduced into the *Aspergillus* mutant strain according to the present invention, a gene encoding a saccharifying enzyme with high heat resistance (for example, a saccharifying enzyme having an activity at 80° C. or more is also preferred. This is due to the fact that by carrying out the saccharification process for the cellulose-based biomass at a relatively high temperature (for example, 50° C. to 80° C.), the efficiency of saccharification can be further enhanced.

As the saccharifying enzyme with high heat resistance, for example, a xylanase derived from *Thermoascus aurantiacus*, a β-xylosidase derived from Thermotoga maritime and the like can be mentioned.

<Production Method of Saccharifying Enzyme>

A method of producing a saccharifying enzyme according to the present invention is characterized in that the transformant according to the present invention is cultured on a solid medium which is used herbaceous biomass as a substrate. Since the transformant according to the present invention is derived by using the AOK27L strain that originally exhibits a high enzyme production yield in solid culture as a parent strain, it can produce the saccharifying enzyme with high yield by solid culture than the transformants produced by using other *Aspergillus oryzae* strains as parent strains.

The solid used as substrate in this method is preferably herbaceous biomass, and more preferably rice straw or corn stover.

The herbaceous biomass may be pretreated by a step which includes maintaining under an acidic condition such as dilute sulfuric acid or under an alkaline such as ammonia.

In other words, a method of producing a saccharifying enzyme of the present invention includes culturing the transformant according to the present invention on a solid medium which is used herbaceous biomass as a substrate. The method may further include pretreating the herbaceous biomass, and may include isolating a saccharifying enzyme by recovering and purifying the cultures.

The culturing on a solid medium, for example, includes adding the transformant according to the present invention (for example, inoculated with $1\times10^5$ to $1\times10^7$ spores) to the pre-treated rice straw of the herbaceous biomass, and then culturing. The culture temperature is preferably 30° C. to 37° C., incubation time is preferably 40 to 72 hours.

It should be noted that the saccharifying enzyme produced by the transformant according to the present invention may be used in the saccharification reaction by bringing the transformant into direct contact with the base, or may be used as a saccharifying enzyme crudely or properly purified from the transformant.

EXAMPLES

Next, the present invention will be described in more detail based on a series of Examples, but the present invention is not limited to the following Examples.

Reference Example 1

The strains of *Aspergillus oryzae* and *Aspergillus awamori* (strain RIB40, strain RIB128, strain AOK20, strain AOK2P, strain AOK27L, strain AOK65, strain AOK139, strain AOK210, strain AOK241, strain AOK1597, strain AOK1505, strain AOK1506, strain AOK1508, strain AOK1509 and strain AOK1510) (all strains were obtained from Akita Konno Co., Ltd.) were compared by calculating the enzyme production yield based on the total amount of the enzyme secreted extracellularly. Here, the term "enzyme production yield" refers to the amount of enzyme produced per the carbon source introduced, and it was calculated by the following formula.

[enzyme production yield]=[total amount of enzyme secreted]/[amount of dextrin was introduced]. Formula:

More specifically, first, rice straw was pulverized to a size so as to pass through a mesh having an opening of 3 mm, and ammonia water at a concentration of 25% by mass based on the dry weight was mixed such that the mass ratio was 1:1. By holding the mixture obtained for 120 hours at room temperature (about 20° C.) and then heating to a temperature of 60 to 80° C. under reduced pressure, ammonia is vaporized and separated to thereby produce ammonia-treated rice straw.

Separately, each *Aspergillus* strain was cultured for 1 week in a Czapek-Dox (CD) medium (containing 3% (wt/vol) dextrin, 0.1% (wt/vol) potassium dihydrogen phosphate, 0.2% (wt/vol) potassium chloride, 0.05% (wt/vol)

magnesium sulfate, 0.001% (wt/vol) iron sulfate and 0.3% (wt/vol) sodium nitrate), thereby preparing a spore suspension.

1 mL of a 10% solution of dextrin (manufactured by Wako Pure Chemical Industries, Ltd.) was added to 1 g of the ammonia-treated rice straw (water content: about 10%), and 0.085 mL of 2M hydrochloric acid (manufactured by Wako Pure Chemical Industries, Ltd.) was further added thereto to adjust the pH to 6, thereby preparing a substrate sample as a base. For the pH measurement, 5 mL of ultrapure water was added to 1 g of the substrate sample, and the pH of the suspended solution was measured.

Next, 5 g of the substrate sample was weighed and placed in a 50 mL volume plastic tube (manufactured by Becton, Dickinson and Company), and was autoclaved at conditions of 121° C. and 15 minutes. The substrate sample following the autoclaving was inoculated with $1\times10^6$ spores, and, after stirring, transferred to a sterile petri dish (manufactured by Asahi Glass Co., Ltd.) and cultured for 40 hours at 30° C. and 95% RH. In addition, at the same time, a sample not inoculated with spores (negative control) was also treated in the same manner.

The total amount of the substrate after cultivation was collected into a 50 mL volume plastic tube, 15 mL of a 0.5% solution of sodium chloride (manufactured by Wako Pure Chemical Industries, Ltd.) was added thereto and stirred, and the resultant was allowed to stand for 2 hours at 4° C. Following standing, the resultant was centrifuged for 10 minutes at 10,000×g at 4° C., and the resulting supernatant was processed with a sterile filter (manufactured by Merck KGaA), thereby obtaining an enzyme solution.

SDS-PAGE was carried out using 10 μL of the thus obtained enzyme solution, and the total amount of secreted enzyme was calculated from the intensity of the resulting bands. The negative control was analyzed by HPLC to calculate the charged amount of dextrin. From the obtained total amount of secreted enzyme and the charged amount of dextrin, the enzyme production yield was calculated based on the aforementioned formula.

FIG. 1 shows the enzyme production yield by each strain. As a result, the AOK27L strain exhibited the highest enzyme production capacity among the *Aspergillus oryzae* strains used for screening, and exhibited a higher enzyme production capacity by about 2-fold compared to that of the *Aspergillus oryzae* strain RIB40, which was commonly used.

Example 1

The pyrG gene was deleted from the AOK27L strain by genetic recombination through a protoplast-PEG method to obtain an *Aspergillus oryzae* strain HO1 (hereinafter, may be abbreviated as the "HO1 strain") exhibiting auxotrophy for uridine and high enzyme productivity in solid culture.

More specifically, first, by using the genomic DNA of the AOK27L strain (obtained from Akita Konno Co., Ltd.) as a template and amplifying the upstream sequence of pyrG gene (SEQ ID NO: 3) with a primer 1 (SEQ ID NO: 1) and primer 2 (SEQ ID NO: 2) and the downstream sequence of pyrG gene (SEQ ID NO: 6) with a primer 3 (SEQ ID NO: 4) and primer 4 (SEQ ID NO: 5) by PCR, respectively, followed by purification, gene fragments of the sequences upstream and downstream of the pyrG gene were obtained. A commercially available DNA polymerase (product name: KOD FX neo, manufactured by Toyobo Co., Ltd.) was used for the PCR, and a commercially available purification kit (product name: QIAquick PCR purification kit, manufactured by QIAGEN) was used for the purification.

Separately, the plasmid pRI910 (manufactured by Takara Bio Inc.) was treated with the restriction enzyme SmaI (manufactured by Takara Bio Inc.) at 30° C. and purified using the aforementioned purification kit to obtain a digested product of the plasmid (gene fragment).

The thus obtained three gene fragments were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pRI-AoΔpyrG.

The PCR amplification was carried out using the primers 1 and 4, a DNA polymerase (product name: KOD-plus-ver.2, manufactured by Toyobo Co., Ltd.) and the obtained plasmid pRI-AoΔpyrG as a template, and the resulting product was purified using the aforementioned purification kit to obtain a gene fragment (AoΔpyrG fragment) for the transformation of *Aspergillus* strains.

Figure 2:
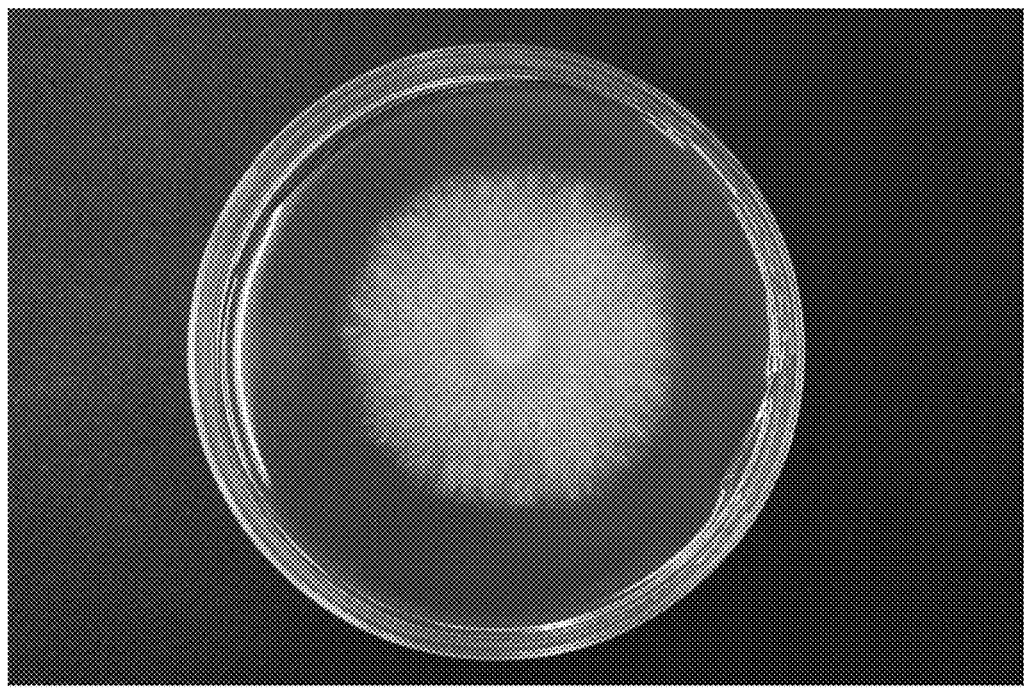
FIG. 2 is a photographic view of a uridine-containing CD plate medium following the incubation of the *Aspergillus oryzae* strain HO1 for 120 hours in Example 1.
Figure 3:
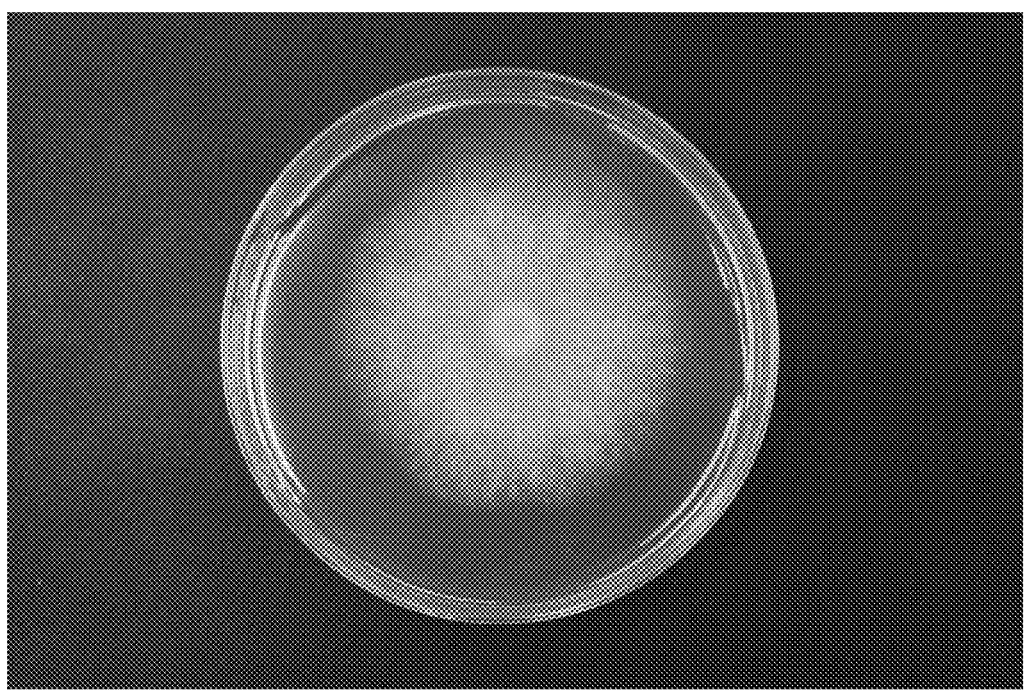
FIG. 3 is a photographic view of a uridine-containing CD plate medium following the incubation of the *Aspergillus oryzae* strain AOK27L for 120 hours in Example 1.

In accordance with the conventional procedure of PEG-calcium method, the AOK27L strain was transformed using the AoΔpyrG fragment. A plate medium (uridine-containing CD plate medium) was prepared by adding, to the CD medium, 5-fluoroorotic acid monohydrate (manufactured by Wako Pure Chemical Industries, Ltd.) to a final concentration of 1 mg/mL and uridine (manufactured by Sigma-Aldrich) to a final concentration of 20 mM, and then a strain which can grow on this plate medium was selected from the processed products of transformation to obtain the HO1 strain which was a pyrG gene-deleted strain. FIGS. 2 and 3 show photographs of uridine-containing CD plate medium after 120 hours of incubation. When cultured on the uridine containing CD plate medium, the HO1 strain (FIG. 2) grew as equally well as the AOK27L strain (FIG. 3) which was the parent strain.

It should be noted that the HO1 strain is a newly produced strain and has excellent properties such that it is suitable for solid culture, enzyme productivity is high and an efficient genetic recombination is also possible. Therefore, the applicant of the present invention has international deposited the HO1 strain to the Patent Microorganisms Depositary (NPDM) of the National Institute of Technology and Evaluation (NITE) (Room No. 122, 2-5-8 Kazusakamatari, Kisarazu, Chiba, Japan) as a new microorganism (date of deposition: Nov. 12, 2013) under the Butapest Treaty. The Accession number is NITE BP-01749, and the strain will be available to the public under the conditions specified in 37 CFR 1.808.

Example 2

A transformant of the HO1 strain producing each enzyme was constructed by introducing each of the cellobiohydrolase (CBH1) gene and β-glucosidase (BGL) gene of *Acremonium cellulolyticus* and endoxylanase (EX) gene of a fungus belonging to the genus *Thermoascus* to the HO1 strain prepared in Example 1.

A transformant (CBH1-producing strain) obtained by introducing the CBH1 gene derived from *Acremonium cellulolyticus* and the pyrG gene derived from *Aspergillus oryzae* into the HO1 strain was prepared in the following manner.

Each gene fragment was obtained by first amplifying, by PCR: a cellobiohydrolase (cbh1) gene (SEQ ID NO: 9) by using the genomic DNA of *Acremonium cellulolyticus* H1 strain as a template and using a primer 21 (SEQ ID NO: 7) and a primer 22 (SEQ ID NO: 8); an enoA promoter gene (SEQ ID NO: 12) by using the genomic DNA of the HO1 strain prepared in Example 1 as a template and a primer 23 (SEQ ID NO: 10) and a primer 24 (SEQ ID NO: 11); and a pyrG gene (SEQ ID NO: 15) by using the same genomic DNA of HO1 strain as a template and a primer 25 (SEQ ID NO: 13) and a primer 26 (SEQ ID NO: 14), respectively, followed by purification. A commercially available DNA polymerase (product name: KOD FX neo, manufactured by Toyobo Co., Ltd.) was used for the PCR, and a commercially available purification kit (product name: QIAquick PCR purification kit, manufactured by QIAGEN) was used for the purification.

Separately, the plasmid pMD20 (manufactured by Takara Bio Inc.) was treated with the restriction enzyme SmaI (manufactured by Takara Bio Inc.) at 30° C. and purified using the aforementioned purification kit to obtain a digested product of the plasmid (gene fragment).

The thus obtained four gene fragments were treated using the In-Fusion (registered trademark) HD Cloning Kit (manufactured by Takara Bio Inc.), and the resultant was used to transform *E. coli* strain HST08 (manufactured by Takara Bio Inc.) to obtain a plasmid pPPD1-CBH1.

The PCR amplification was carried out using the primers 23 and 26, a DNA polymerase (product name: KOD-plus-ver.2, manufactured by Toyobo Co., Ltd.) and the obtained plasmid pPPD1-CBH1 as a template, and the resulting product was purified using the aforementioned purification kit to obtain a gene fragment (pyrG-CBH1 fragment) for the transformation of *Aspergillus* strains.

In accordance with the conventional procedure of PEG-calcium method, the HO1 strain was transformed using the pyrG-CBH1 fragment. A medium was prepared in the same manner as in Example 1 by adding, to the CD medium, 5-fluoroorotic acid monohydrate to a final concentration of 1 mg/mL and uridine to a final concentration of 20 mM, and then a strain which could grow on this medium was selected from the processed products of transformation to obtain a CBH1-producing strain.

The thus obtained CBH1-producing strain was allowed to form spores by being cultured on the CD plate medium for 1 week, and the resultant was collected using 0.01% POLYSORBATE 20 (manufactured by Wako Pure Chemical Industries Ltd.) to obtain a spore suspension.

Then, 100 mL of a PD liquid medium (containing 2% (wt/vol) dextrin, 1% (wt/vol) polypeptone, 0.1% (wt/vol) casamino acid, 0.5% (wt/vol) potassium dihydrogen phosphate, 0.05% (wt/vol) magnesium sulfate and 0.1% (wt/vol) sodium nitrate) was poured into a 500 mL Erlenmeyer flask, and the aforementioned spores were inoculated thereto to a final spore concentration of $1 \times 10^4$ spores/mL. Then, the incubation was carried out in a liquid culture for 3 days at 30° C. to obtain a culture liquid of the CBH1-producing strain in which the target enzyme CBH1 was expressed and secreted into the culture medium.

A transformant (BGL-producing strain) obtained by introducing the BGL gene derived from *Acremonium cellulolyti-cus* and the pyrG gene derived from *Aspergillus oryzae* into the HO1 strain was prepared in the same manner as that for the CBH1-producing strain with the exception that a gene fragment (SEQ ID NO: 18) of the BGL gene obtained by PCR using a primer 27 (SEQ ID NO: 16), a primer 28 (SEQ ID NO: 17) and a chemically synthesized DNA fragment of the BGL gene derived from *Acremonium cellulolyticus* (all synthesized by Takara Co., Ltd.) as a template was used instead of a cbh1 gene fragment obtained using the primers 21 and 22.

A transformant (EX-producing strain) obtained by introducing the EX gene derived from a fungus belonged to the genus *Thermoascus* and the pyrG gene derived from *Aspergillus oryzae* into the HO1 strain was prepared in the same manner as that for the CBH1-producing strain with the exception that a gene fragment of the EX gene (SEQ ID NO: 21) obtained by PCR using a primer 29 (SEQ ID NO: 19), a primer 30 (SEQ ID NO: 20) and a chemically synthesized DNA fragment of the EX gene derived from *Thermoascus aurantiacus* (totally synthesized by Takara Co., Ltd.) as a template was used instead of a cbh1 gene fragment obtained using the primers 21 and 22.

By culturing the obtained BGL-producing strain and the EX-producing strain in the same manner as that for the CBH1-producing strain, a culture liquid of the BGL-producing strain in which the target enzyme BGL was expressed and secreted into the culture medium and a culture liquid of the EX-producing strain in which the target enzyme EX was expressed and secreted into the culture medium were obtained, respectively.

Figure 4:
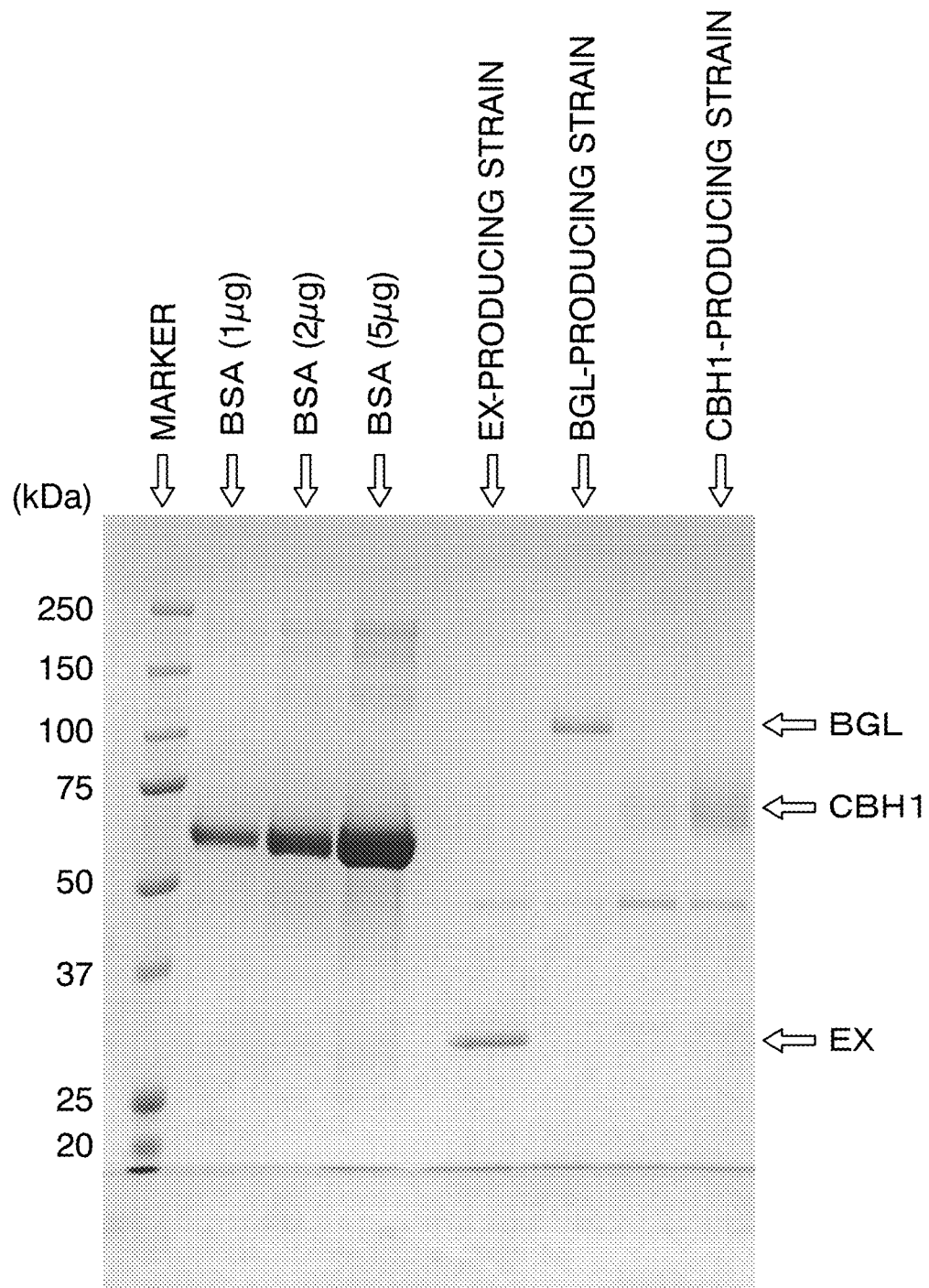
FIG. 4 is a diagram showing the result of an SDS-PAGE analysis of the enzyme samples prepared from the transformants obtained by introducing each enzyme gene into the *Aspergillus oryzae* strain HO1 in Example 2.

Each enzyme in the supernatant (enzyme sample) of the culture liquids of the CBH1-producing strain, BGL-producing strain, and EX-producing strain was confirmed by the SDS-PAGE analysis. 1, 2, and 5 μg of BSA were run simultaneously in order to use as the standards of the protein concentration. FIG. 4 shows the result of SDS-PAGE analysis of the enzyme sample (10 μL) and BSA. As a result, it was confirmed that CBH1 having a molecular weight of about 75 kDa was included in the culture supernatant of the CBH1-producing strain, BGL having a molecular weight of about 110 kDa was included in the culture supernatant of the BGL-producing strain, and EX having a molecular weight of about 30 kDa was included in the culture supernatant of the EX-producing strain.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

[Accession Number]
NITE BP-01749
[Sequence Listing]

What is claimed is:

1. A transformant obtained by introducing a pyrG gene and a saccharifying enzyme gene into *Aspergillus oryzae* strain H01 (accession number: NITE BP-01749), wherein said saccharifying enzyme gene is at least one gene selected from the group consisting of a cellobiohydrolase gene derived from *Acremonium cellulolyticus*, a β-glucosidase gene derived from *Acremonium cellulolyticus*, an endoxylanase gene derived from a fungus belonging to the genus *Thermoascus*, an arabinofuranosidase gene derived from *Acremonium cellulolyticus* and a glucuronidase gene derived from *Acremonium cellulolyticus*.

2. The transformant according to claim 1, wherein the pyrG gene and the saccharifying enzyme gene are incorporated into a chromosome.

3. A method of producing a saccharifying enzyme, the method comprising culturing the transformant described in claim 1 by solid culturing.

4. The method of producing a saccharifying enzyme according to claim 3, wherein the solid culturing is carried out using rice straw or corn stover.

* * * * *

SEQUENCE LISTING

```
<160> NUMBER OF SEQ ID NOS: 21

<210> SEQ ID NO 1
<211> LENGTH: 41
<212> TYPE: DNA
<213> ORGANISM: Artificial Sequence
<220> FEATURE:
```

<223> OTHER INFORMATION: Description of Artificial Sequence:Primer 1

<400> SEQUENCE: 1
tcgagctcgg taccccaga ggtgacttta tccaagattc c                41

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:Primer 2

<400> SEQUENCE: 2
cccgggcaat tgccgcgaaa aattaaattg aatc              34

<210> SEQ ID NO 3
<211> LENGTH: 917
<212> TYPE: DNA
<213> ORGANISM: Aspergillus oryzae AOK27L
<220> FEATURE:
<223> OTHER INFORMATION: Upstream sequence of pyrG gene

<400> SEQUENCE: 3
ccagaggtga ctttatccaa gattccttca cgacactgga agaactgctt gaagagctgc    60
ctgagtcaat cagcttcaat atcgagataa gtaggttata tgctgccact ggtggttctc   120
cacttgcggg agacaaagct aacaacgtcc caatgaagag tacccaggc ttcatgaagc    180 tatagaagca ggtgtagcac cagtggctat tgaaatcaac accttcatcg acaaagcgct   240
tgagagactc ttttcttacg gcaacaaaaa acgaccatt atcctatcct catttactcc    300
cgagatctgc attttattgg ccatcaaaca acagacgtac cctgtgatgt tcatcactaa   360
tgccggcaag cctccagtta cggatcgaga gatgagggct gccagcatac agtccgctgt   420
tcgatttgcc aagaggtgga atttatctgg ccttgtcttt gcatctgagg cgctggtaat   480
gtgccccagg cttgtcagat atgttcaacg atcaggattg atctgtggat cctatggatc   540
tcagaacaat ataccagaaa atgcgaaggt aagtgcttct atattgatcc ttagtgcttt   600
caaactgtga tgtagaagtt gctcggtagc tgattaaata ttctagaccc aagccgctgc   660
tggaattgac attattatgg ccgatagggt tgggcttatt gctatgtccc tgaaaggata   720
tcaaaagcag gcaaaaagcc aggcataatc cccgcgtgga cggtacccta aggataggcc   780
ctaatcttat ctacatgtga ctgcatcgat gtgtttggtc aaaatgaggc atgtggctca   840
ccccacaggc ggagaaacgt gtggctagtg catgacagtc cctccatag attcaattta    900 attttttcgcg gcaattg                                              917

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence:Primer 3

<400> SEQUENCE: 4
cggcaattgc ccggggtagt ggtggatacg tactcctttt atg                43

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence:Primer 4

<400> SEQUENCE: 5
ctctagagga tccccgttgc ggatcttgct gcttg                          35

<210> SEQ ID NO 6
<211> LENGTH: 1000
<212> TYPE: DNA
<213> ORGANISM: Aspergillus oryzae AOK27L
<220> FEATURE:
<223> OTHER INFORMATION: Downstream sequence of pyrG gene

<400> SEQUENCE: 6
gtagtggtgg atacgtactc cttttatggc agtatgtcgc aagtatgatg cgatttataa     60
attcagcact cgaaatgact actactatgt gtctacgaca gatacccctct ccgtacgaat    120 aagacacctg cctcgatata tggacaaatt caaaatcagg gtcaagggtc atgtttcaaa    180
gtcacaacaa tctccaacat agacgagaat ttgtaccgga gtgtctgaag gtgcagctgg    240
agattggtct attttcttag agtggggtat cactaatgta cagtcggtca ctatcgtaca    300
aacaatcaca attatataca agatttccca ccacccccta ctctaacacg cacaattat     360 ccatcgagtc agagcctagc caccatttgg tgctctcgta gagaccaaag tataatcctg    420
atccgacagc ggccataaac gtgttgatag cacaccctcg gaatagtcct ctcgggccat    480
ctgttcgtac aatctcccgt acggtattga tcatcctttt cttctgaggt gcagttgtat    540
ctgcagcatc gagcatgatt cgtgtccgga ccatatccat gggtgctgtc aagacactag    600
ctataccgcc cgagaccgca gcacttattg cggctgtcgc tgcagcctct ccgattgtcg    660
aatgggcctc tttctttcca tactctcttg gtctttctag caccttctct cgatctccga    720
atctatattc aaaaattcga taccgaaaag actcgtacag aggcatctga atcgccgaca    780
ctggcaagct atgcgccaca agagccgggt atccgctcca aagctgtcta gggttgataa    840
acttcttgaa agctagccgt gtcgctttct gggctacacc acctacctt cccccagcta    900 caggtgctga tgcgtctgga tggtgtgatt ggatcatctg cgcgttgtgt tttaatgcat    960
cagccggagc aaagactccg caagcagcaa gatccgcaac                         1000

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:Primer 21

<400> SEQUENCE: 7
gttcttccag tgtcgctaca aacattgaga gtagtaaggg ttcacg               46

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:Primer 22

<400> SEQUENCE: 8
atgtctgcct tgaactcttt caatatgtac                                30

<210> SEQ ID NO 9
<211> LENGTH: 1590
<212> TYPE: DNA
<213> ORGANISM: Acremonium cellulolyticus
<220> FEATURE:

<223> OTHER INFORMATION: cbh1 gene

<400> SEQUENCE: 9

| | | | | | |
|---|---|---|---|---|---|
| atgtctgcct | tgaactcttt | caatatgtac | aagagcgccc | tcatcttggg | ctccttgctg | 60 |
| gcaacagctg | gtgctcagca | aattggtact | tataccgctg | aaacccatcc | ctctctgagc | 120 |
| tggtctactt | gcaaatcggg | tggtagctgc | accacaaact | ccggtgccat | tacgttagat | 180 |
| gccaactggc | gttgggtcca | tgtgtcaat | accagcacca | actgctacac | tggcaacact | 240 |
| tggaatagcg | ccatctgcga | cactgatgca | tcctgtgcac | aggactgtgc | tctcgatggt | 300 |
| gctgactact | ctggcacgta | cggtatcact | acctccggca | actcattgcg | cctgaacttc | 360 |
| gttaccggtt | ccaacgtcgg | atctcgtact | tacctgatgg | ccgataacac | ccactaccaa | 420 |
| atcttcgact | tgttgaacca | ggagttcacc | ttcaccgtcg | atgtctccca | cctcccttgc | 480 |
| ggtttgaacg | gtgccctcta | cttcgtgacc | atggatgccg | acggtggcgt | ctccaagtac | 540 |
| cccaacaaca | aggccggtgc | tcagtacggt | gttggatact | gtgactctca | atgccctcgt | 600 |
| gacttgaagt | tcatcgctgg | tcaggccaac | gttgagggc | ggacgccctc | ctccaacaac | 660 |
| gccaacactg | gaattggcaa | tcacggagct | tgctgcgcgg | agcttgatat | ctgggaggca | 720 |
| aacagcatct | cagaggcctt | gactcctcac | ccttgcgata | cacccggtct | atctgtttgc | 780 |
| actactgatg | cctgcggtgg | tacctacagc | tctgatcgtt | acgccggtac | ctgcgaccct | 840 |
| gatggatgtg | acttcaaccc | ttaccgtctt | ggtgtcactg | acttctacgg | ctccggcaag | 900 |
| accgttgaca | ccaccaagcc | ctttaccgtt | gtgactcaat | cgtcactaa | cgacggtacc | 960 |
| tccaccggtt | ccctctccga | gatcagacgt | tactacgttc | agaacggcgt | tgtcatcccc | 1020 |
| cagccttcct | ccaagatctc | cggaatcagc | ggaaatgtca | tcaactccga | ctactgcgct | 1080 |
| gctgaaatct | ccacctttgg | cgggactgcc | tccttcagca | aacacggtgg | cttgacaaac | 1140 |
| atggccgctg | gtatggaagc | tggtatggtc | ttggtcatga | gtttgtggga | cgactacgcc | 1200 |
| gtcaacatgc | tctggctcga | cagcacctac | cctacaaacg | cgactggtac | ccccggtgcc | 1260 |
| gctcgtggta | cctgcgctac | cacttctggg | gaccccaaga | ccgttgaagc | acaatccggc | 1320 |
| agctcctatg | tcaccttctc | tgacattcgg | gttggtcctt | tcaattctac | gttcagcggt | 1380 |
| ggttctagca | ccggtggcag | cactactact | accgccagcc | gcaccaccac | cacctcggcc | 1440 |
| tcttccacct | ctacttccag | cacctctact | ggcactggag | tcgctggtca | ctggggtcag | 1500 |
| tgtggtggcc | agggctggac | tggtcctacc | acctgtgtta | gtggaaccac | atgcaccgtc | 1560 |
| gtgaacccctt | actactctca | atgtttgtag | | | | 1590 |

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:Primer 23

<400> SEQUENCE: 10
gttcaaggca gacattttga cgagctgcgg aattggtc     38

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:Primer 24

<400> SEQUENCE: 11

```
tcgagctcgg tacccagatc tcgcggcagg gttgac                                36
```

<210> SEQ ID NO 12
<211> LENGTH: 734
<212> TYPE: DNA
<213> ORGANISM: Aspergillus oryzae AOK27L
<220> FEATURE:
<223> OTHER INFORMATION: eno A promoter gene

<400> SEQUENCE: 12

```
agatctcgcg gcagggttga cacagttgac agagagctca gccagcgaga gtcacagaag     60
actgatgagc cccaccattt cattggaaag attcggagg acgaggtcga gagcttttgc    120
cggggtagag gacgaggatg gtacaagaac tagaccttc caactttaat tgttgacacc    180
tatttaattc tctccttctt ctttatttta tttttcattt ctccaacgac gactgtctca    240
ttactagtct actagtaact ctgtcttatc gtcatctccc ataggtgagt ttggttgttt    300
tgtttccact gagatcatga cctcctccta ccccaccatc ccactatttt tgttacggta    360
gccatgaccc ctccatggca aagagagagg aggacgagga cgatcaggaa actgtgtctc    420
gccgtcatac cacaatcgtg ttatcctgat tgacatcttc ttaaatatcg ttgtaactgt    480
tcctgactct cggtcaactg aaattggatc tccccaccac tgcctctacc ttgtactccg    540
tgactgaacc atccgatcat tcttttttggg tcgtcggtga acacaacccc cgctgctagt    600
ctccttccaa caccgatcca gaattgtttt gattttccat tcccttcgtt tatatctgtc    660
gtctctcctc cctttccgtc tcttttcttc cgtcctccaa gttagtcgac tgaccaattc    720
cgcagctcgt caaa                                                      734
```

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence:Primer 25

<400> SEQUENCE: 13

```
ggatatcgga tccccggtgg tgggaaatct tgtatataat tgtgattg                  48
```

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Primer 26

<400> SEQUENCE: 14

```
cgacactgga agaactgctt gaag                                            24
```

<210> SEQ ID NO 15
<211> LENGTH: 2300
<212> TYPE: DNA
<213> ORGANISM: Aspergillus oryzae AOK27L
<220> FEATURE:
<223> OTHER INFORMATION: pyrG gene

<400> SEQUENCE: 15

```
cgacactgga agaactgctt gaagagctgc ctgagtcaat cagcttcaat atcgagataa     60
gtaggttata tgctgccact ggtggttctc cacttgcggg agacaaagct aacaacgtcc    120
caatgaagag taccccaggc ttcatgaagc tatagaagca ggtgtagcac cagtggctat    180
```

```
tgaaatcaac accttcatcg acaaagcgct tgagagactc ttttcttacg gcaacaaaaa    240
acggaccatt atcctatcct catttactcc cgagatctgc attttattgg ccatcaaaca    300
acagacgtac cctgtgatgt tcatcactaa tgccggcaag cctccagtta cggatcgaga    360
gatgagggct gccagcatac agtccgctgt tcgatttgcc aagaggtgga atttatctgg    420
ccttgtcttt gcatctgagg cgctggtaat gtgcccagg cttgtcagat atgttcaacg     480
atcaggattg atctgtggat cctatggatc tcagaacaat ataccagaaa atgcgaaggt    540
aagtgcttct atattgatcc ttagtgcttt caaactgtga tgtagaagtt gctcggtagc    600
tgattaaata ttctagaccc aagccgctgc tggaattgac attattatgg ccgatagggt    660
tgggcttatt gctatgtccc tgaaaggata tcaaaagcag gcaaaagcc aggcataatc      720 cccgcgtgga cggtacccta aggataggcc ctaatcttat ctacatgtga ctgcatcgat    780
gtgtttggtc aaaatgaggc atgtggctca ccccacaggc ggagaaacgt gtggctagtg    840
catgacagtc ccctccatag attcaattta attttttcgcg gcaattgtcg tgcagtttgt   900
atctacattt cattccatat atcaagagtt agtagttgga catcctgatt attttgtcta    960
attactgaaa actcgaagta ctaacctact aataagccag tttcaaccac taagtgctca   1020
tttatacaat atttgcagaa ccccgcgcta ccctccatc gccaacatgt cttccaagtc    1080
gcaattgacc tacagcgcac gcgctagcaa gcaccccaat gcgctcgtaa agaagctctt   1140
cgaggttgcc gaggccaaga aaccaatgt caccgtttcc gccgacgtga caaccaccaa    1200
agagctgctg gatttggctg accgtatgcg caccggggat gccacttaca tgtgatctag   1260
taatggttaa tggtggatta tataacagga ctcggtccgt acattgccgt gatcaaaact   1320
cacatcgata tcctctccga tttcagcgaa gaaaccatca ccggtctgaa ggcccttgca   1380
gagaagcaca atttcctcat cttcgaagat cgcaagttca tcgatatcgg aaacacagtc   1440
caaaagcagt accatggcgg cactctgcgt atctctgagt gggcccacat catcaactgc   1500
agtattctgc ccggtgaggg tatcgtcgag gctctggccc agactgcttc ggccgaggac   1560
ttcccctacg gctccgagag gggccttttg atccttgcgg agatgacctc caagggatct   1620
ttggctaccg gtcaatatac tacttcttct gttgactatg ctcggaagta taagaagttt   1680
gtgatgggat tcgtctcgac acgtcacctt ggcgaggttc agtctgaagt tagctcgcct   1740
tcggaggagg aagattttgt cgtcttcacg acaggtgtca acctctcctc gaagggtgac   1800
aagctgggac agcagtacca aactcctgag tcggctgttg gacgcggtgc cgactttatt   1860
attgctggcc gtggaattta tgctgctcct gatcccgtgg aggcggcgaa gcagtaccag   1920
aaggagggat gggatgcata cctgaagcgt gttggtgcgc aataagtagt ggtggatacg   1980
tactcctttt atggcagtat gtcgcaagta tgatgcgatt tataaattca gcactcgaaa   2040
tgactactac tatgtgtcta cgacagatac cctctccgta cgaataagac acctgcctcg   2100
atatatggac aaattcaaaa tcagggtcaa gggtcatgtt tcaaagtcac acaatctcc    2160 aacatagacg agaatttgta ccggagtgtc tgaaggtgca gctggagatt ggtctatttt   2220
cttagagtgg ggtatcacta atgtacagtc ggtcactatc gtacaaacaa tcacaattat   2280
atacaagatt tcccaccacc                                               2300
```

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence:Primer 27

<400> SEQUENCE: 16
gttcttccag tgtcgtcact ggaggcactg ggagtac                              37

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:Primer 28

<400> SEQUENCE: 17
atgtactccg cctttctgct c                                               21

<210> SEQ ID NO 18
<211> LENGTH: 2442
<212> TYPE: DNA
<213> ORGANISM: Acremonium cellulolyticus
<220> FEATURE:
<223> OTHER INFORMATION: BGL gene

<400> SEQUENCE: 18

```
atgtactccg cctttctgct cctcctggcc tccgccaccc ctatcgtttc cgcccagtcc    60
gcctcctggt ccgccgccta ctctaaggct accgccgctc tctccaagct ctcccagaac   120
gataagatcg gcatggtcac cggcgtcggc tggggcaagg gtccttgcgt cggcaacacc   180
gctgccccti ccggcatctc cttcccatcc ctctgcatcc aggattcccc cctcggcgtc   240
cgctacgcca accctgtcac cgctttccct gccggcacca cgccggcat gacctgggat   300
cgcactctca tgaaccagcg cggtgccgcc ctcggagctg agtctaaggg tctgggcgtc   360
catgtccagc tcggccctgt cgctggccct tcggcaagda tcgctcaggg tggtcgcggc   420
tgggagggct tcggtactga tccttacctc tccggcgtcg ccatgatcga aaccatctcc   480
ggcatgcagt cctccggcac ccaggcctgc gccaagcact acatcggcaa cgagcaagag   540
ctgaaccgcg agtccatgtc ctccaacatc gatgatcgca cctgcacga gctgtacctc   600
tggccttteg ccgatgccgt ccgcgccaac gtcgcctccg tcatgtgctc ctacaaccag   660
atcaacggca ccttcagctg cgagaacgag gaatccatga ccggcatcct caagaccgag   720
ctgggctttc ctggctacat catgtccgat tgggatgccc agcataccac cgtcacctcc   780
gccaactccg gcctcgatat gaccatgcct ggctccgatt actccgatac ccttcctcc   840
gtcctctggg ccagaaacct cgccaacgcc atctcctccg gccaggtcgc tcagtcccgc   900
ctcgatgata tggtcaccc catcctcgcc gcctggtatc tcgtcggcca ggatcagggc   960
ttccctgccg tcgccttcaa ctcctggacc ggcggtcagg cctccgtcaa cgtcacctcc  1020
aaccataacc aggtcgctcg cgccgtcgcc cgcgattcca tcgtcctgct caagaacacc  1080
aactccaccc tgcctctcaa caagccttcc tctatcgcca tcatcggcac cgatgcccag  1140
accaacccti ccggccctaa cgcctgcacc gatcgcggtt gcgataccgg caccctcgcc  1200
atgggttggg gctctggaac ctgccagttc ccttacctca ccgatcctct caccgccatc  1260
aagacccgcg ctgcctccga tggcaccacc atcaccacct ccatctccga taacggctcc  1320
gccggtgcct ccgtcgccca gtctgctgag tacgccatcg tgttcatcaa ctccgattcc  1380
ggcgagggct acatcaccgt cgagggcgtc gctggcgatc gcaacaacct cgatccttgg  1440
cattccggca acgccctcgt ccagtccgtc gccgccgtca acaagaaaac catcgtcgtc  1500
atccattctg tcggccctgt catcctcgaa accatcctcg cccagcctaa cgtcgtcgct  1560
```

```
gtcgtctggg ccggcattcc tggccaagag tccggttccg ccctcaccga tatcctctac    1620
ggctccaccg ccccttccgg caagctcacc tacactatcg ccaagcaggc cagcgattac    1680
ggcaccgctg tcgtctctgg ctccgataac taccctgagg gcctcttcat cgattaccgc    1740
catttcgata agtccaacat cgagcctcgc tacgagttcg gctacggcct ctcctacacc    1800
accttcggct acaccaacct cgccatcgat atcaccgtca gcaccggccc taccaccggc    1860
cagattgtcc ctggcggccc ttccgatctc ttcgagtccg tcggcaccgt caccgtccag    1920
gtcgccaaca ccggctccgt cgccggttct gaggtcgccc agctctacat cggcctccct    1980
agctccgctc cttccagccc tcctaagcag ctccgcggct tcgataagct ctccctcgcc    2040
gctggcgctt ccggaaccgc taccttcgat ctgacccgcc gtgatctctc ctactgggat    2100
gtctccaagc agaagtgggt cgtcccttcc ggcgccttca ctgtctacgt cggcgcctcc    2160
tctcgcgata tccgcctcca gggcaccttc acccctggcg gcagctccac tacctccacc    2220
atcacctcca gcaagacctc caccaccatc tctaccteeg tcactaccte ctccagcacc    2280 accgccaaga ctaccactac ctcttccacc accagcagcc cggtcctac ccagaccect     2340 tacggccagt gcggcggtca gggttggact ggtcctaccg tctgctcctc cggctggacc    2400
tgcaaggtca ccaaccagtg gtactcccag tgcctccagt ga                       2442

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence:Primer 29

<400> SEQUENCE: 19
gttcttccag tgtcgtcact gctggagatc ctggac                              36

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Primer 30

<400> SEQUENCE: 20
atggtccgcc ctaccatcct                                                20

<210> SEQ ID NO 21
<211> LENGTH: 990
<212> TYPE: DNA
<213> ORGANISM: Thermoascus aurantiacus
<220> FEATURE:
<223> OTHER INFORMATION: EX gene

<400> SEQUENCE: 21
atggtccgcc ctaccatcct cctcacctcc ctcctcctcg cccctttcgc cgccgcctct    60
cctatccttg aggagcgcca ggctgcccag tccgtcgatc agctcatcaa ggcccgcggc    120
aaggtctact cggcgtcgc caccgatcag aaccgcctca ccaccggcaa gaacgccgcc    180
atcatccagg ccgatttcgg ccaggtcacc cctgagaact ccatgaagtg ggatgccacc    240
gagcctttcc cagggcaactt caacttcgcc ggcgccgatt acctcgtcaa ctgggcccag    300
cagaacggca agctcatccg cggccatacc ctcgtctggc attcccagct cccttcctgg    360
gtctcctcca tcaccgataa gaacacectc accaacgtca tgaagaacca tatcaccacc    420
ctcatgaccc gctacaaggg caagatccgc gcctgggatg tcgtcaacga ggccttcaac    480
```

```
gaggatggct ccctccgcca gaccgtcttc ctcaacgtca tcggcgagga ttacatccct    540
atcgccttcc agaccgcccg cgccgccgat cctaacgcca agctctacat caacgattac    600
aacctcgatt ccgcctccta ccctaagacc caggccatcg tcaaccgcgt caagcagtgg    660
cgcgccgccg gcgtccctat cgatggcatc ggctcccaga cccatctctc cgctggccag    720
ggcgcttccg tcctccaggc tctccctctc ctcgcttccg ccggcacccc tgaagtcgcc    780
atcaccgagc tcgatgtcgc cggcgcctcc tccaccgatt acgtcaacgt cgtcaacgcc    840
tgcctcaacg tccagtcctg cgtcggcatc accgtctggg gcgtcgccga tcctgattcc    900
tggcgcgcct ccaccacccc tctcctcttc gatggcaact tcaaccctaa gcctgcctac    960
aacgccatcg tccaggatct ccagcagtga                                     990
```